United States Patent
Gil et al.

(10) Patent No.: US 10,206,631 B2
(45) Date of Patent: Feb. 19, 2019

(54) AUTOMOTIVE KEY DEVICE, STEERING WHEEL DOCKING STATION, AND SYSTEM INCLUDING THE AUTOMOTIVE KEY DEVICE AND THE STEERING WHEEL DOCKING STATION

(71) Applicant: HUINNO CO., LTD., Seoul (KR)

(72) Inventors: Yeong Joon Gil, Busan (KR); Min Yong Shin, Gyeonggi-do (KR)

(73) Assignee: HUINNO CO., LTD., Seoul (KR)

( * ) Notice: Subject to any disclaimer, the term of this patent is extended or adjusted under 35 U.S.C. 154(b) by 0 days.

(21) Appl. No.: 15/637,620

(22) Filed: Jun. 29, 2017

(65) Prior Publication Data

US 2017/0367661 A1 Dec. 28, 2017

Related U.S. Application Data

(63) Continuation of application No. 14/864,413, filed on Sep. 24, 2015.

(30) Foreign Application Priority Data

Jan. 27, 2015 (KR) .................. 10-2015-0012855
Mar. 6, 2015 (KR) .................. 10-2015-0031979
(Continued)

(51) Int. Cl.
*A61B 5/00* (2006.01)
*A61B 5/0488* (2006.01)
(Continued)

(52) U.S. Cl.
CPC ............ *A61B 5/7278* (2013.01); *A61B 5/002* (2013.01); *A61B 5/0006* (2013.01);
(Continued)

(58) Field of Classification Search
CPC .................. B60R 25/25; B60R 99/00; B60W 2040/0872; B60W 2040/0818;
(Continued)

(56) References Cited

U.S. PATENT DOCUMENTS

2012/0101690 A1* 4/2012 Srinivasan ........... A61B 5/0408
701/45
2012/0112879 A1* 5/2012 Ekchian ................ A61B 5/117
340/5.53
(Continued)

FOREIGN PATENT DOCUMENTS

JP 2007-203913 A 8/2007

*Primary Examiner* — Muhammad N Edun
*Assistant Examiner* — Jerold Murphy
(74) *Attorney, Agent, or Firm* — Mintz Levin Cohn Ferris Glovsky and Popeo, P.C.; Kongsik Kim; Derek E. Constantine (57) ABSTRACT provided is an automotive key device connected, in the form of a holder, to a mechanism of opening or shutting an automotive door or merged with the mechanism of opening or shutting the automotive door. The automotive key device includes an electrocardiogram (ECG) sensor having a first body signal electrode and a second body signal electrode and a contact terminal electrically connected to the ECG sensor. The contact terminal is configured to serve as a passage for electrical connection with devices within a vehicle. A steering wheel docking station and a system configured to include the steering wheel docking station and the automotive key device are also provided.

17 Claims, 7 Drawing Sheets

(30) Foreign Application Priority Data

| Mar. 6, 2015 | (KR) | 10-2015-0031980 |
|---|---|---|
| Mar. 9, 2015 | (KR) | 10-2015-0032676 |
| Apr. 10, 2015 | (KR) | 10-2015-0051015 |

(51) Int. Cl.

| *A61B 5/1455* | (2006.01) |
|---|---|
| *B60R 25/25* | (2013.01) |
| *A61B 5/0205* | (2006.01) |
| *A61B 5/024* | (2006.01) |
| *A61B 5/0408* | (2006.01) |
| *A61B 5/0432* | (2006.01) |
| *A61B 5/0402* | (2006.01) |
| *A61B 5/0404* | (2006.01) |
| *A61B 5/04* | (2006.01) |
| *B62D 1/04* | (2006.01) |
| *B62D 1/06* | (2006.01) |
| *G06F 19/00* | (2018.01) |
| *G16H 40/67* | (2018.01) |
| *A61B 5/021* | (2006.01) |

(52) U.S. Cl.
CPC .......... *A61B 5/0008* (2013.01); *A61B 5/0022* (2013.01); *A61B 5/0205* (2013.01); *A61B 5/02055* (2013.01); *A61B 5/02108* (2013.01); *A61B 5/02433* (2013.01); *A61B 5/04* (2013.01); *A61B 5/0402* (2013.01); *A61B 5/0404* (2013.01); *A61B 5/0408* (2013.01); *A61B 5/0432* (2013.01); *A61B 5/04085* (2013.01); *A61B 5/0488* (2013.01); *A61B 5/14551* (2013.01); *A61B 5/14552* (2013.01); *A61B 5/4266* (2013.01); *A61B 5/6893* (2013.01); *A61B 5/6898* (2013.01); *A61B 5/725* (2013.01); *A61B 5/742* (2013.01); *B60R 25/25* (2013.01); *B62D 1/046* (2013.01); *B62D 1/06* (2013.01); *G06F 19/00* (2013.01); *G16H 40/67* (2018.01); *A61B 5/021* (2013.01); *A61B 5/02416* (2013.01); *A61B 2503/22* (2013.01); *A61B 2560/0468* (2013.01); *A61B 2562/227* (2013.01)

(58) Field of Classification Search
CPC ......... B60W 2540/22; B60W 2540/28; B60W 40/08; G06K 2009/00939; G06K 9/00885
See application file for complete search history.

(56) References Cited

U.S. PATENT DOCUMENTS

| 2014/0163349 | A1* | 6/2014 | Amitai | A61B 5/7475 600/393 |
|---|---|---|---|---|
| 2014/0276112 | A1* | 9/2014 | Fung | A61B 5/024 600/479 |
| 2014/0316227 | A1* | 10/2014 | Rake | B62D 1/046 600/323 |

* cited by examiner

AUTOMOTIVE KEY DEVICE, STEERING WHEEL DOCKING STATION, AND SYSTEM INCLUDING THE AUTOMOTIVE KEY DEVICE AND THE STEERING WHEEL DOCKING STATION

CROSS-REFERENCES TO RELATED APPLICATIONS

This application is a continuation pursuant to 35 U.S.C. § 371, of 14/864,413 filed on Sep. 24, 2015, which claims priority to Korean Application No. 10-2015-0051015, filed Apr. 10, 2015, Korean Application No. 10-2015-0032676, filed Mar. 9, 2015, Korean Application No. 10-2015-0031979, filed Mar. 6, 2015, Korean Application No. 10-2015-0031980, filed Mar. 6, 2015, and Korean Application No. 10-2015-0012855, filed Jan. 27, 2015. The entire contents of the aforementioned patent applications are incorporated herein by this reference.

TECHNICAL FIELD

The present invention relates to an automotive key device, a steering wheel docking station, and a system including the automotive key device and the steering wheel docking station.

BACKGROUND

Recently, the rapid development of scientific technology has improved the quality of life of the entire humanity and caused many changes in the medical environment. After a medical image, such as X-ray, computed tomography (CT), functional magnetic resonance imaging (fMRI), etc., is taken at a hospital, it may take several hours or days before the medical image can be interpreted. However, a picture archiving and communication system (PACS) was introduced that allows for a medical image to be sent to the monitor screen of a radiologist by the PACS and then immediately interpreted. In addition, a lot of ubiquitous healthcare-related medical devices that enable a user to check his or her blood glucose and blood pressure without visiting a hospital have been introduced. Therefore, patients with high blood glucose or high blood pressure are using these medical devices at their home or office.

In particular, high blood pressure is a major risk factor for various diseases, and its prevalence rate is increasing. There has been a need for a system that can continuously measure blood pressure and provide the measured blood pressure in real time. As an example of a method for measuring blood pressure, ubiquitous healthcare (u-Health) has been used. In u-Health, a blood pressure measuring sensor is inserted into the pulmonary artery of a patient with a chronic heart disease to measure blood pressure in real time, and the measured blood pressure is sent to the patient's doctor using wireless communication. The doctor may remotely monitor any change in the blood pressure of the patient's pulmonary artery and may send a prescription to the patient. This technology can dramatically reduce patients' visits to hospitals. However, although the technology has the advantage of measuring blood pressure continuously and accurately, blood pressure is measured in an invasive manner in this technology. The technology thus entails a difficult medical procedure and runs the risks of arterial damage and possible contamination.

Therefore, interest has remained in a system that can measure blood pressure in a non-invasive manner and in real time without inserting a blood pressure measuring sensor into an artery blood vessel. Additional research has been conducted on methods of monitoring blood pressure in the ubiquitous environment and providing measured blood pressure to a user as a bio-feedback so that the user can monitor and may be able to control his or her blood pressure. A technology that employs a method of measuring blood pressure by attaching a cuff to an arm has also been used. In this technology, however, someone (a patient or another person) has to operate a blood pressure measuring device each time a blood pressure measurement value needs to be obtained. Therefore, continuous measurement of blood pressure is difficult.

In particular, in order to quickly inform a patient of the risk of high blood pressure so that the patient can receive emergency treatment within a short time, a technology is needed that can measure blood pressure continuously and inform a patient of the blood pressure measurement result in real time to enable the patient himself or herself to prevent and/or manage high blood pressure. A system may be used that includes a non-invasive sensor, which can measure signals such electrocardiogram (ECG), photoplethysmography (PPG) and saturation of peripheral oxygen ($SpO_2$), in a device wearable on a human body. The system can monitor blood pressure in real time by estimating a blood pressure level by processing the above signals. A method of estimating blood pressure based on measured body signals is disclosed in Korean Patent Application Nos. 2013-116158 and 2013-116165, incorporated herein by reference in their entirety.

Figure 1:
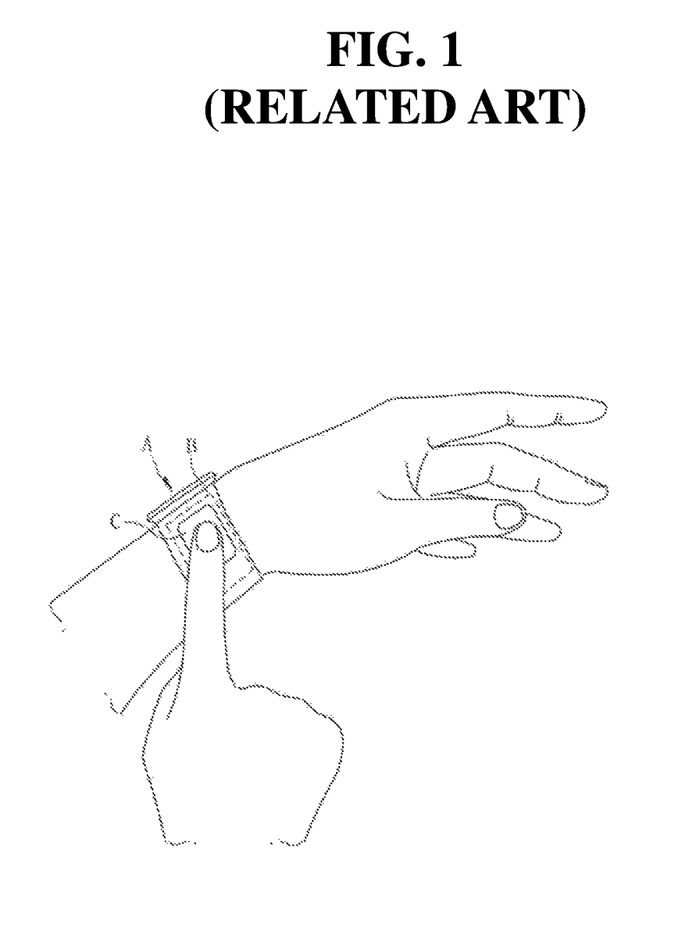
FIG. 1 illustrates a blood pressure measuring method in the related art.

FIG. 1 illustrates related art in the form of an embodiment of a blood pressure measuring method. Referring to FIG. 1, a main body of a blood pressure measuring device includes a display A, a first electrode B, and a second electrode C. The first electrode B for body signal measurement is installed on a back of the main body (e.g. an inner surface that contacts a wrist wearing the main body of the blood pressure measuring device), and he second electrode C for body signal measurement is installed on a front of the main body (e.g. an outer surface that does not contact the wrist wearing the main body of the blood pressure measuring device). If the user touches the second electrode C with a part (such as a finger) of his or her body while the first electrode B contacts a user's wrist wearing the main body, the user's ECG signal can be measured by the first electrode B and the second electrode C. Further, using a measuring terminal (not illustrated in FIG. 1), the blood pressure measuring device can be connected to sensors for measuring PPG and $SpO_2$ signals. Then, a blood pressure level calculated based on the measured body signals may be displayed on the display A for the user.

Hereinafter, ECG, PPG and $SpO_2$ (i.e. examples representative of "multiple body signals" referred to throughout) will be described in more detail. The "multiple body signals" may include other body signals in addition to or instead of the above signals, though. An ECG is a waveform that represents the vector sum of action potentials generated by a special excitatory and conductive system. That is, the ECG is a vector sum signal, measured using electrodes attached onto the human body, of action potentials generated by each component of the heart such as sinoatrial (SA) node, atrioventricular (AV) node, His bundle, bundle branches, Purkinje fibers, etc. For example, an ECG signal can be obtained using a standard limb lead method.

A PPG is a pulse wave signal measured in peripheral blood vessels when blood ejected during ventricular systole is delivered to the peripheral blood vessels. A PPG signal can be measured using optical characteristics of biological tissue. For example, a PPG sensor (a photo sensor) that can measure a pulse wave signal may be attached to a location (such as a fingertip or a tip of a toe) where the peripheral blood vessels are distributed. Then, the PPG sensor may measure a PPG signal by converting a change (a volume change) in the blood flow rate of the peripheral blood vessels into a change in the amount of light. The PPG signal can be measured by irradiating red light generated by a light-emitter of the PPG sensor to the human body and observing a change in the amount of light reflected by the human body and then received by a light receiver. Generally, information such as pulse transit time (PTT) or pulse rave velocity (PWV) is extracted by analyzing the correlation between a PPG signal and an ECG signal, instead of the PPG signal only, and cardiovascular diseases are diagnosed based on the extracted information. A characteristic point may be obtained by performing a quadratic differential on a PPG signal, and PTT and PWV signals may be extracted by measuring a time interval from a peak (R wave) of an ECG signal. Then, the extracted PTT and PWV signals are used to diagnose the state of blood vessels, hardening of the arteries, peripheral circulatory disturbance, etc.

$SpO_2$ is a body signal indicating oxygen content in hemoglobin from among various components of blood. $SpO_2$ can be measured by sequentially irradiating red light and infra-red light to an area of peripheral blood vessels of the human body in each period and observing a change in the amount of light reflected by the human body and then received by a light receiver. For example, $SpO_2$ can be measured using the PPG sensor (the photo sensor) described above.

SUMMARY

The present disclosure relates to enabling a driver to easily measure his or her body signals by including multi-body signal measurers in an automotive key device always carried by the driver. The present disclosure also relates to enabling the driver to measure his or her body signals more easily and accurately by connecting the automotive key device to a vehicle, more specifically, to a docking station of a steering wheel on which both hands of the driver are placed naturally while driving. The present disclosure additionally relates to utilizing the driver's measured body signals for various purposes using a system formed by devices, such as a navigation device, an automotive personal computer (PC), a communicator, etc. provided within the vehicle, together with the automotive key device and the steering wheel docking station.

However, objectives of the present invention are not restricted to the one set forth herein. Objectives of the present invention will become more apparent to one of ordinary skill in the art to which the present invention pertains by referencing the detailed description of the present invention given below According to an aspect of an exemplary embodiment the present invention, an automotive key device is provided that may be connected, in the form of a holder, to a mechanism of opening or shutting an automotive door or may be merged with the mechanism of opening or shutting the automotive door. The automotive key device may include an electro-cardiogram (ECG) sensor that includes a first body signal electrode and a second body signal electrode; and a contact terminal that may be electrically connected to the ECG sensor, where the contact terminal functions as a passage for electrical connection with devices within a vehicle. The automotive key device may include a photoplethysmogra-phy (PPG) sensor and a saturation of peripheral oxygen ($SpO_2$) sensor, where the PPG sensor and the $SpO_2$ sensor are electrically connected to the contact terminal. In addition, the automotive key device may include a memory for storing measured body signals.

According to another aspect of an exemplary embodiment of the present invention, a steering wheel docking station may be provided to which the automotive key device is connected. The steering wheel docking station may include one or more replacement electrodes that replace functions of one or all of the first body signal electrode and the second body signal electrode of the automotive key device. The replacement electrodes may transmit signals front a driver's hands on a steering wheel to the automotive key device through the contact terminal such that the driver's ECG information can be obtained. The replacement electrodes may be disposed at locations where the driver's hands are placed while driving. Therefore, while the driver is driving, the driver's body signals can be received naturally by the replacement electrodes.

The steering wheel docking station may include a receptacle into which the automotive key device is inserted. One or all of the first body signal electrode and the second body signal electrode of the automotive key device may be exposed when the automotive key device is inserted into the receptacle. In this case, one replacement electrode may be provided to obtain body signals in place of one of the first body signal electrode and the second body signal electrode of the automotive key device. The other body signal electrode whose functions are not replaced by the replacement electrode from among the first body signal electrode and the second body signal electrode of the automotive key device may be used to eliminate a common phase in order to remove noise generated while the vehicle is being driven.

In the steering wheel docking station, alternatively, none of the first body signal electrode and the second body signal electrode of the automotive key device may be exposed when the automotive key device is inserted into the receptacle. In this case, two replacement electrodes may be provided to obtain body signals in place of the first body signal electrode and the second body signal electrode of the automotive key device, respectively. When the driver's body signal information collected while the automotive key device is connected to the steering wheel docking station is transmitted to the automotive key device via the contact terminal, driving related information measured by sensors within the vehicle or information obtained from sensors installed in the driver's smart phone or other devices may also be transmitted to the automotive key device via the contact terminal. This information (such as the vehicle's speed, temperature, altitude, the vehicle's location data in the form of, for example, global positioning system or GPS data, etc. at the time of collecting body signals) may be stored in the automotive key device in association with the driver's body signal information and utilized accordingly.

According to another aspect of an exemplary embodiment of the present invention, a system may be provided including the automotive key device and the steering wheel docking station. The system may include an automotive navigation device or PC that is electrically connected to the steering wheel docking station. In this system, body signal information obtained by the automotive key device may be provided to the automotive navigation device or PC via the steering wheel docking station and stored in the automotive navigation device or PC or used as a basis for providing other body signal information through an arithmetic operation. The automotive key device may further include a PPG sensor and a SpO$_2$ sensor, wherein the PPG sensor and the SpO$_2$ sensor are electrically connected to the contact terminal. In this case, the automotive navigation device or PC may calculate the driver's blood pressure information based on the body signal information including ECG, PPG and SpO$_2$ information obtained from the automotive key device and store the calculated blood pressure information. In the system, the automotive navigation device or PC may include a display. Therefore, the body signal information obtained from the automotive key device or the blood pressure information calculated based on the body signal information may be displayed on the display.

The system may include a communicator. Therefore, the body signal information obtained from the automotive key device or the blood pressure information calculated based on the body signal information may be transmitted to an external server via the communicator. When the driver's body signal information collected while the automotive key device is connected to the steering wheel docking station is transmitted to the automotive key device via the contact terminal, driving related information measured by sensors within the vehicle or information obtained from sensors installed in the driver's smart phone or other devices may also be transmitted to the automotive key device via the contact terminal and stored in the automotive key device in association with the driver's body signal information. In this case, when the body signal information obtained from the automotive key device or the blood pressure information calculated based on the body signal information is transmitted to the external server via the communicator, the information stored in association with the body signal information may also be transmitted to the external service via the communicator. Therefore, the environment at the time of collecting body signals can be analyzed from more diverse aspects.

The system including the communicator may receive a feedback signal to the body signal information or the blood pressure information calculated based on the body signal information from the external server via the communicator. In this case, the system may alert the driver or put the vehicle in an emergency driving mode based on the feedback signal and transmit the feedback signal to a server of an emergency rescue center together with GPS information of the vehicle so that an emergency situation can be dealt with more effectively.

Other additional elements can further be provided within the scope of the present invention.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Although exemplary embodiments may be described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, exemplary embodiments of the present invention will be described in detail with reference to the accompanying drawings to enable those skilled in the art to easily implement the invention.

For a clear understanding of the present invention, a detailed description of components and features irrelevant to the present invention will be omitted. Like reference numerals refer to like components throughout the specification. In addition, the shape and size of each component illustrated in the drawings are merely intended for ease of description, but the present invention is not necessarily limited to the shape and size. That is, specific shapes, structures and characteristics described herein may be implemented as modified from one embodiment to another without departing from the spirit and scope of the invention. Furthermore, it shall be understood that the locations or arrangements of individual components within each embodiment may also be modified without departing from the spirit and scope of the invention. Therefore, the following detailed description is not to be taken in a limiting sense, and the scope of the invention is to be taken as encompassing the scope of the appended claims and all equivalents thereof.

Automotive Key Device

Examples of a device for opening or shutting an automotive door are provided herein as follows. For example, a mechanical key may be manufactured by mechanical machining and may open and/or shut an automotive door by being mechanically fitted into the lock of the automotive door. Another example is a combination of a mechanical key and a wireless transmission device that can transmit a command for opening and/or shutting an automotive door. Typically, the wireless communication device is connected, in the form of a holder, to the mechanical key.

Another example is a smart key. The smart key may or may not include a mechanical key. A system that goes a step further than the wireless transmission device may be installed inside a vehicle. The system may sense whether a driver or a passenger has a smart key and, based on the detection result, actuate an automotive door to open or shut automatically when the driver or the passenger touches the door. In addition, the system may actuate the vehicle to start by a motion, such as pressing a start button, when sensing the smart key instead of when the mechanical key is inserted into a lock connected to a starting device. The mechanical key may exist in the smart key only for emergency purposes. That is, the mechanical key may be housed within the smart key. In usual cases, the door may be opened and/or shut using only the smart key. However, when the door cannot be opened or shut using the smart key because, for example when a battery of the smart key has been completely discharged, the mechanical key may be separated from the smart key, and the door may be opened or shut using the mechanical key. The mechanical key can also be omitted entirely.

An "automotive key device" may be implemented as the above-described automotive door opening or shutting device including electrical/electronic mechanisms of opening or shutting an automotive door and mechanisms of accomplishing functions of the present disclosure. The "automotive key device" may be provided separate from the automotive door opening or shutting device and can be implemented in the form of a holder connected to the automotive door opening or shutting device. The automotive key device may include sensors for measuring multiple body signals such as electrocardiogram (ECU), photoplethysmography (PPG) and saturation of peripheral oxygen (SpO$_2$). Using these sensors, the automotive key device can monitor a user's health condition in real time.

Figure 2:
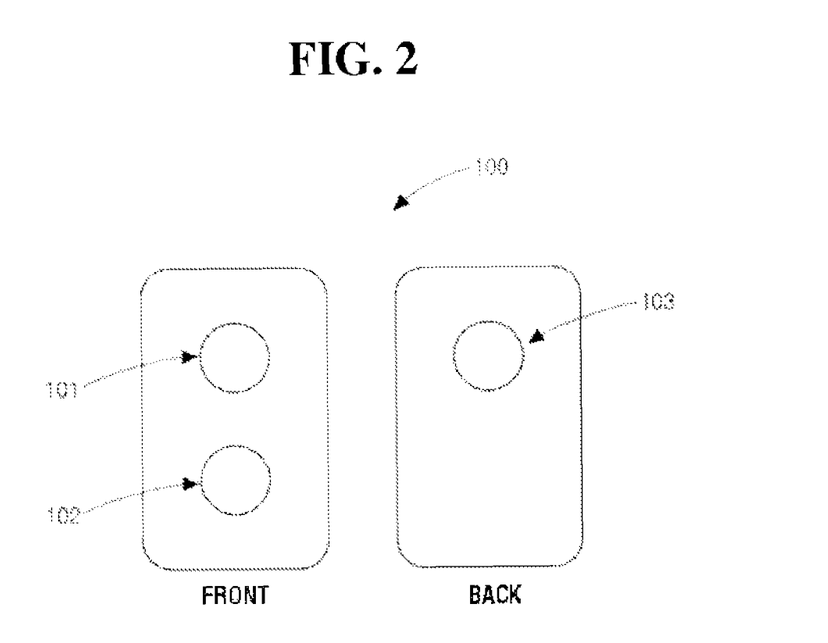
FIG. 2 illustrates an automotive key device according to an exemplary embodiment of the present invention.

FIG. 2 illustrates an automotive key device 100 according to an exemplary embodiment. The front of the automotive key device 100 is illustrated on the left side of FIG. 2, and the back of the automotive key device 100 is illustrated on the right side of FIG. 2. Upper and lower circles in the front of the automotive key device 100 represent a first body signal electrode 101 and a second body signal electrode 102, respectively. These electrodes 101 and 102 form an ECG sensor. The ECG may be measured in a state where a finger of a hand is in contact with one of the two body signal electrodes 101 and 102 and where a finger of the opposite hand is in contact with the other electrode. An ECG measurement principle using two body signal electrodes has already been disclosed and is described in detail in Korean Patent Application Nos. 2013-416158 and 2013-116165, incorporated herein.

A circle is shown in the middle of the back of the automotive key device 100 of FIG. 2. The circle may represent a contact terminal 103 that allows the automotive key device 100 to exchange signals with electrical/electronic devices inside a vehicle when the automotive key device 100 is connected to a steering wheel docking station 200. While only one contact terminal 103 is illustrated in FIG. 2, a plurality of contact terminals 103 may be provided. The contact terminal 103 not only allows the automotive key device 100 to exchange signals with the electrical/electronic devices within the vehicle but also allows a battery included in the auto key device 100 to be charged. The battery included in the automotive key device 100 may be a rechargeable secondary cell. The battery may be discharged as the automotive key device 100 performs the function of opening or shutting an automotive door and the function of measuring a driver's body signals. When the automotive key device 100 is connected to the vehicle, the battery may be charged by a power source inside the vehicle through the contact terminal 103. In this case, the functions of the automotive key device 100 may be utilized semi-permanently without replacement of the battery of the automotive key device 100.

The first and second body signal electrodes 101 and 102 illustrated in FIG. 2 may be used to measure the ECG as described above. Also, the first and second body signal electrodes 101 and 102 may be connected to a sensor so as to measure body signals, e.g., body temperature. Additional embodiments in which sensors for measuring other body signals such as PPG and SpO$_2$ are further included in the automotive key device 100 are also within the scope of the present invention. If body signals such as PPG and SpO$_2$ can be obtained using PPG and SpO$_2$ sensors included in the automotive key device 100 together with the ECG sensor, real-time blood pressure level information can be obtained using a unique blood pressure calculation method disclosed in Korean Patent Application Nos. 2013-116158 and 2013-116165, incorporated herein.

The automotive key device 100 may include a storage memory not illustrated). Therefore, if the driver's body signals are measured only by the automotive key device 100, when the automotive key device 100 is connected to the steering wheel docking station 200 after the measurement, data about the measured body signals stored in the storage memory of the automotive key device 100 may be transmitted to a navigation device, a personal computer (PC), etc. of the vehicle. The usage of the transmitted data will be described in detail later. Receivers, communicators, memory, processors, sensors, modules, and/or any units may be operated by a controller having a memory and a processor.

Steering Wheel Docking Station

Figure 3:
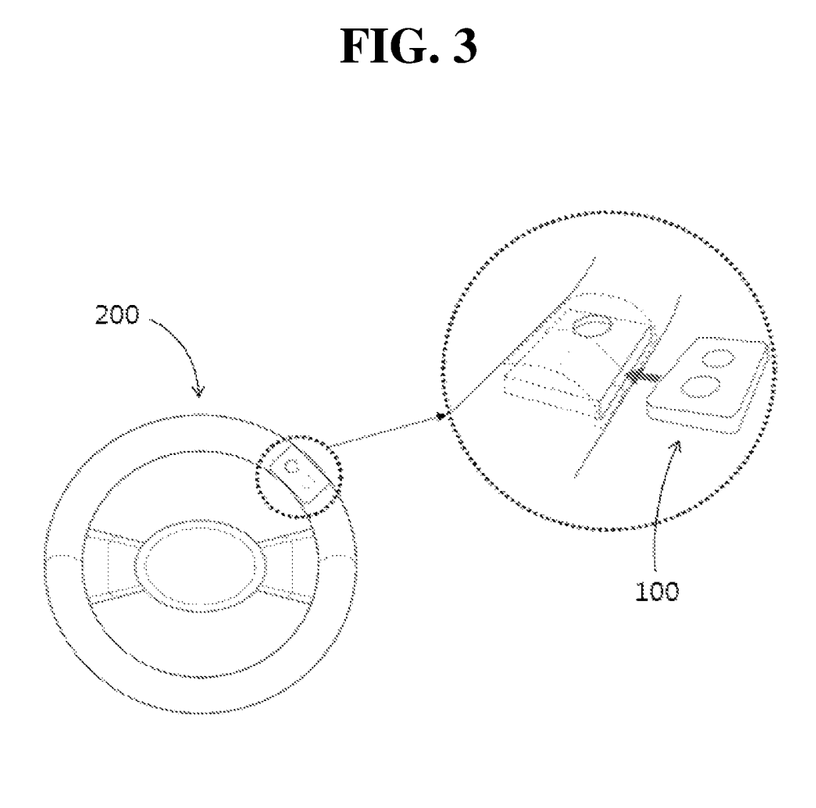
FIG. 3 illustrates a steering wheel docking station according to an exemplary embodiment of the present invention.

FIG. 3 illustrates a steering wheel docking station 200 according to an exemplary embodiment. More specifically, FIG. 3 illustrates the configuration of a steering wheel docking station 200 to which the automotive key device 100 is connected and the way the automotive key device 100 and the steering wheel docking station 200 are connected. The steering wheel docking station 200 is formed in a steering wheel at a location to which the automotive key device 100 may be connected. In some embodiments (e.g., embodiments of FIGS. 4 and 6), when the automotive key device 100 is connected to the steering wheel docking station 200, any one or all of the first and second body signal electrodes 101 and 102 of the automotive key device 100 may be used to receive a driver's body signals. In this case, the steering wheel docking station 200 may be provided at any one of two locations where both hands of the driver are placed naturally when the driver holds the steering wheel. In FIG. 3, the steering wheel docking station 200 is provided in the steering wheel at a location where the driver's right hand is placed.

The contact terminal 103 of the automotive key device 100 is provided on the back of the automotive key device 100 as described above. Therefore, when the automotive key device 100 is connected to the steering wheel docking station 200, the contact terminal 103 of the automotive key device 100 contacts a corresponding contact terminal provided on the steering wheel docking station 200. Accordingly, the contact terminals are electrically connected to each other. The steering wheel docking station 200 may further include a mechanical connector that can keep the automotive key device 100 and the steering wheel docking station 200 connected mechanically as well. The mechanical connector may be, for example, a sliding insertion device. That is, a groove having a predetermined depth may be provided in the steering wheel docking station 200, and the automotive key device 100 may be inserted into the grove in a vertical or horizontal direction. Another example of the mechanical connector may be a magnet-based coupling connector. However, the mechanical connector is not limited to the above examples, and any known unit that can keep the automotive key device 100 and the steering wheel docking station 200 connected unless they are intentionally disconnected can be used.

In the embodiment of FIG. 3, the steering wheel docking station 200 provided inside the steering wheel includes an insertion groove at a right side thereof. The automotive key device 100 can be inserted into the steering wheel docking station 200 as the device 100 is slid from the right to the left. The steering wheel docking station 200 can be provided not only inside the steering wheel as in the embodiment of FIG. 3 but also in a housing attached onto a surface of the steering wheel without departing from the scope of the present invention.

In a state where the automotive key device 100 is electrically connected to the steering wheel docking station 200, the first and second body signal electrodes 101 and 102 of the automotive key device 100 may be entirely or partially exposed. In the embodiment of FIG. 3, an opening may be provided at a location where the first body signal electrode 101 is located in an upper surface of the steering wheel in a state where the automotive key device 100 is inserted into the steering wheel docking station 200 provided inside the steering wheel. Therefore, when the driver holds the steering wheel naturally, the driver's finger may contact the first body signal electrode 101 of the automotive key device 100.

Figure 4:
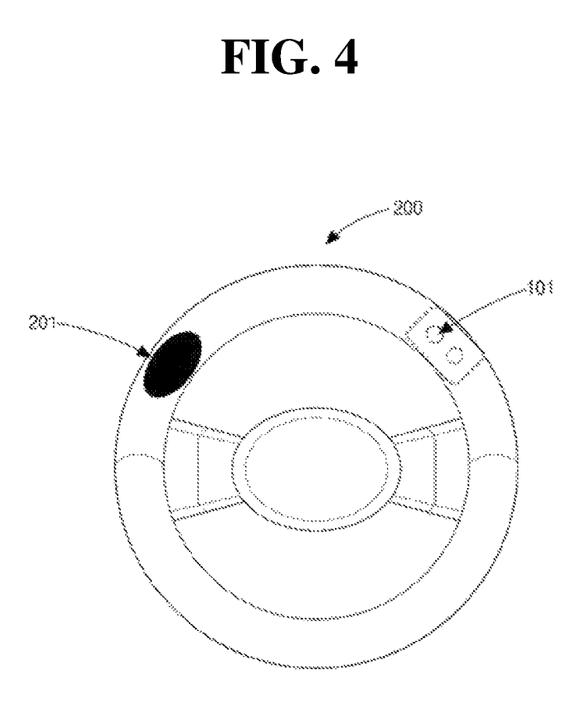
FIGS. 4 through 6 illustrate various exemplary embodiments in which functions of a body signal electrode are replaced in a state where an automotive key device of the present invention is connected to a sleeting wheel docking station.
Figure 5:
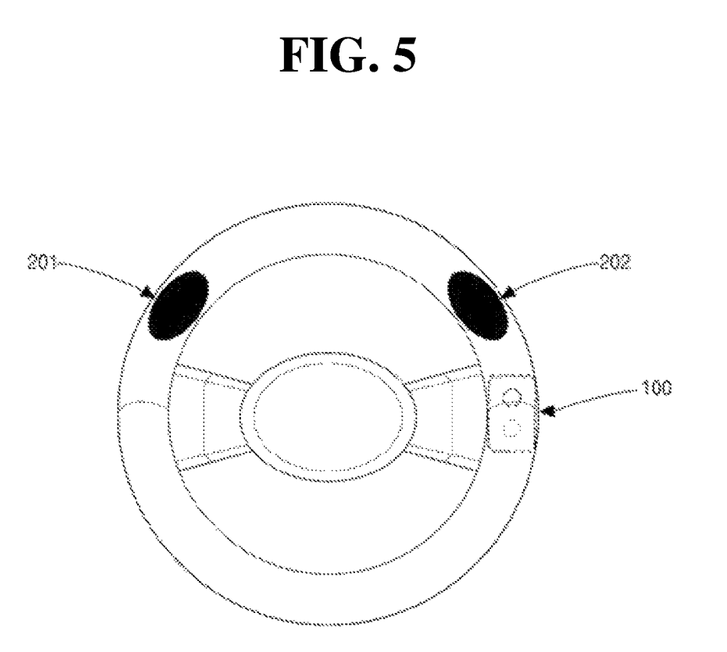
Figure 6:
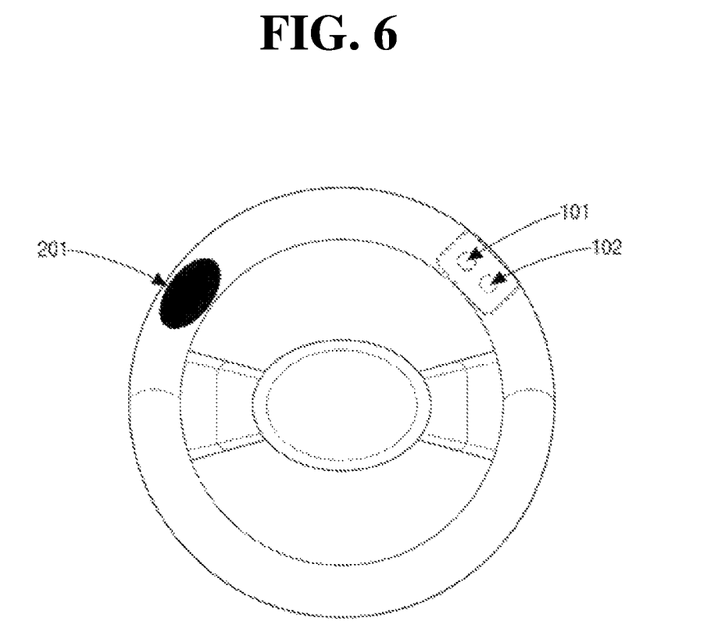
Figure 7:
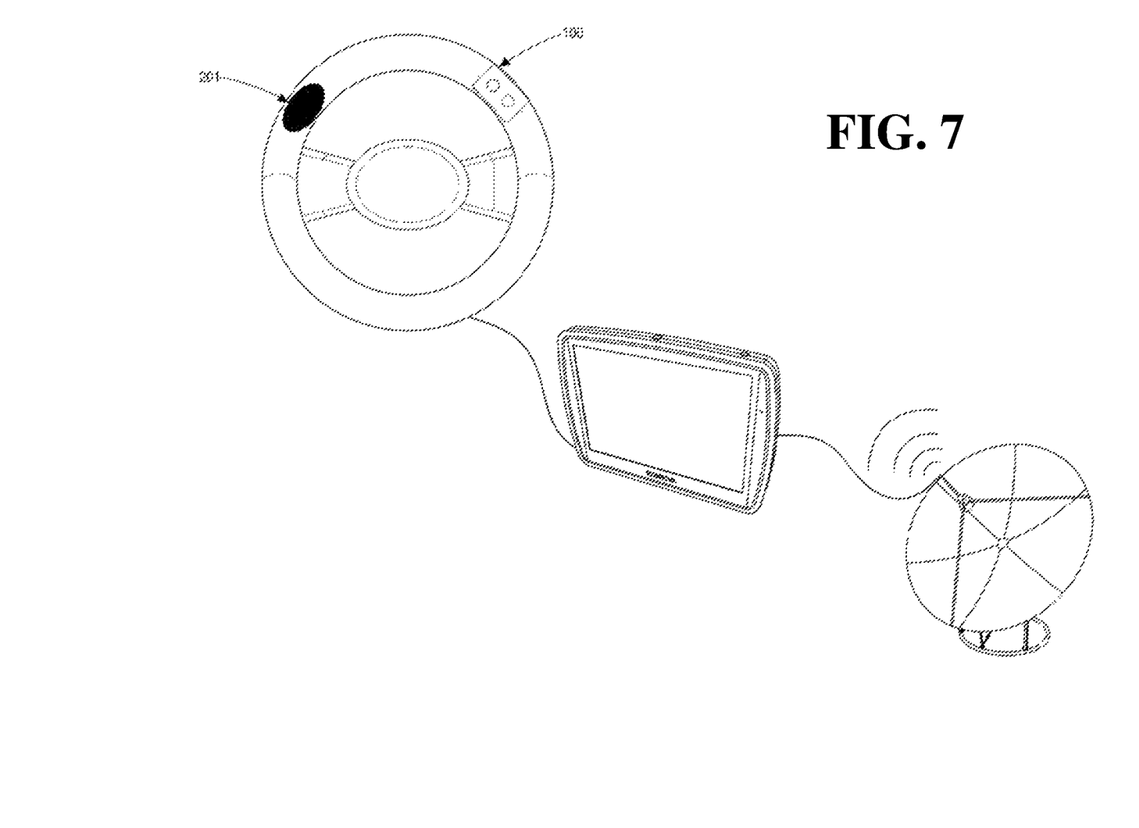
FIG. 7 illustrates a system including an automotive key device and a steering wheel docking station according to an exemplary embodiment of the present invention.

FIGS. 4 through 6 illustrate exemplary cases where functions of a body signal electrode are replaced in a state where the automotive key device 100 is connected to the steering wheel docking station 200. The functional replacement of the body signal electrode is intended to make the measurement of body signals easier when the driver holds the steering wheel with both hands. The functional replacement of the body signal electrode can be implemented in various exemplary cases and embodiments described below.

In a first exemplary embodiment as illustrated in FIG. 4, a first replacement electrode 201 may be placed on the left side of the steering wheel to receive body signals of the heft hand, and one of the first and second body signal electrodes 101 and 102 of the automotive key device 100 may be provided on the right side of the steering wheel and may receive body signals of the right hand. The term "replacement electrode" denotes an electrode to which functions of the first and second body signal electrodes 101 and 102 provided in the automotive key device 100 are transferred. In this embodiment, when the automotive key device 100 is connected to the steering wheel docking station 200, one of the exposed first and second body signal electrodes 101 and 102 of the automotive key device 100 may be kept activated as a body signal electrode, and the other electrode may be deactivated as a body signal electrode. In addition, the functions of the deactivated body signal electrode may be performed by the first replacement electrode 201 on the left side of the steering wheel. The first replacement electrode 201 may be provided in the steering wheel at a location where the driver's left hand is placed naturally. The first replacement electrode 201 may be connected to the automotive key device 100 by electrical wiring inside the steering wheel and the contact terminal 103 of the automotive key device 100. The left hand's body signals measured by the first replacement electrode 101 may be provided to a body signal sensor included in the automotive key device 100, and information about various body signals (e.g. ECG) that can be measured by electrodes can be obtained by the automotive key device 100.

In a second exemplary embodiment as illustrated in FIG. 5, when the automotive key device 100 is connected to the steering wheel docking station 200, all of the first and second body signal electrodes 101 and 102 of the automotive key device 100 may be activated, and a first replacement electrode 201 provided on the left side of the steering wheel and a second replacement electrode 202 provided on the right side of the steering wheel may function as electrodes for inputting body signals of the left and right hands, respectively. In this embodiment, when the automotive key device 100 is connected to the steering wheel docking station 200, the device 100 may be completely inserted into the steering wheel and thus may not be exposed at all. Here, a location where the automotive key device 100 is installed in the steering wheel may be different from the location in the first embodiment. In the first embodiment, because an electrode of the automotive key device 100 may function as a body signal electrode, the automotive key device 100 may be placed at a location where the driver's hand are placed naturally while driving. In the second embodiment, however, because the first and second body signal electrodes 101 and 102 of the automotive key device 100 are all deactivated, there is no need for the automotive key device 100 to be placed at a location where the driver's hands are placed naturally. Therefore, the automotive key device 100 may be completely inserted into a groove formed at an appropriate location in the steering wheel, such that the device 100 is not exposed at all. The driver's body signals input from the first and second replacement electrodes 201 and 202 respectively provided on the left and right sides of the steering wheel of the steering wheel docking station 200 nay be provided to a sensor included in the automotive key device 100 via the electrical wiring inside the steering wheel and the contact terminal 103 of the automotive key device 100. Therefore, information about various body signals (e.g. ECG) that can be measured by electrodes may be obtained b the automotive key device 100.

In a third embodiment as illustrated in FIG. 6, all of the first and second body signal electrodes 101 and 102 of the automotive key device 100 may be activated. However, only one of the first and second body signal electrodes 101 and 102 may be used to input body signals, and a first replacement electrode 201 provided on the left side of the steering wheel may be used as another electrode for inputting body signals. Of the two electrodes 101 and 102 of the automotive key device 100, an electrode not used to input body signals may be used for other purposes, for example, for eliminating a common phase. While a vehicle is being driven, noise can be generated. Therefore, if the electrode not used to input body signals is used to eliminate the common phase, the noise generated by the vehicle being driven can be effectively removed. In this case, all of the first and second body signal electrodes 101 and 102 may be exposed in a state where the automotive key device 100 is connected to the steering wheel docking station 200. As in the first embodiment, the first replacement electrode 201 may be provided in the steering wheel at a location where the driver's left hand is placed naturally while driving and may be connected to the automotive key device 100 by the electrical wiring inside the steering wheel and the contact terminal 103 of the automotive key device 100. Therefore, the left hand's body signals measured by the first replacement electrode 201 may be provided to the sensor included in the automotive key device 100, and information about various body signals (e.g. ECG) can be measured by the automotive key device 100.

When the automotive key device 100 collects the driver's body signals while being connected to the steering wheel docking station 200, driving related information (such s the vehicle's speed, temperature, altitude, the vehicle's location data such as GPS data, etc. at the time of collecting body signals) measured by sensors within the vehicle may be provided to the automotive key device 100. In addition, information obtained not only from the sensors within the vehicle but also from sensors installed in the driver's smart phone or other electronic devices may be transmitted to the automotive key device 100. Body signal information and information about the situation at the time of collecting body signals may be stored and utilized in association with each other. This storage and usage can increase the value of the collected body signal information for practical use.

System Including an Automotive Key Device and a Steering Wheel Docking Station

The automotive key device 100 and the steering wheel docking station 200 described above may form a system together with another electronic device and a communication device.

A display device and an automotive navigation device or PC having storage and calculation functions may be installed within a vehicle. A driver's various body signals may be input by the first and second body signal electrodes 101 and 102 of the automotive key device 100 by one of the first and second body signal electrodes 101 and 102 of the automotive key device 100 and a replacement electrode of a steering wheel, or by the first and second replacement electrodes 201 and 202 respectively provided on the left and right sides of the steering wheel in a state where the first and second body signal electrodes 101 and 102 of the automotive key device 100 are deactivated. Values of these body signals may be read by a body signal sensor of the automotive key 100 and recorded by the storage memory optionally included in the automotive key device 100.

The values of the body signals measured by the automotive key device 100 cannot only be recorded and managed by the storage memory of the automotive key device 100 but also be transmitted to a device (such as an automotive navigation device or PC) including a display and a storage memory via the steering wheel docking station 200 after the automotive key device 100 is electrically connected to the steering wheel docking station 200 by the contact terminal 103. Accordingly, the values of the body signals measured by the automotive key device 100 may be stored and managed by the storage memory of the device, and the values recorded at each time point may be displayed on the display for the driver. The automotive navigation device or PC that forms the system together with the automotive key device 100 and the steering wheel docking station 200 may provide values of body signals that may be measured directly by the body signal sensor as described above. In addition, the automotive navigation device or PC having the calculation function can provide a value of another body signal that can be measured or estimated by performing an arithmetic operation on the above body signals using a certain algorithm.

As mentioned, a unique method of calculating a blood pressure level based on measured body signals such as ECG, PPG and $SpO_2$ is disclosed in Korean Patent Application Nos. 2013-116158 and 2013-116165, incorporated herein. If this method of calculating a blood pressure level is performed by a processor such as an automotive navigation device or PC that forms the system together with the automotive key device 100 and the steering wheel docking station 200, the system both calculate a driver's blood pressure level in real time and inform the driver of the calculated blood pressure level as well as store and manage the calculated blood pressure level using a storage memory included in the system and display a change in the blood pressure level at each time point. The system can be configured to include a communicator. In this case, the system that stores and manages changes in the driver's various body signal information such as ECG, PPG, $SpO_2$, body temperature, and blood pressure can additionally function as a server.

The system functioning as a server may transmit the driver's body information (e.g., blood pressure level) obtained in real time while driving to a hospital through the communicator. If the hospital determines that it is dangerous for the driver to continue driving based on the body information, the hospital may transmit this information to a vehicle system so that the vehicle system can transmit a warning message to the driver. In some cases, the vehicle system may put the vehicle in an emergency control mode. The system functioning as a server may inform an emergency rescue center of an emergency situation through the communicator together with GPS data of the vehicle, so that the emergency rescue center can properly respond to the emergency situation.

When the automotive key device 100 collects the driver's body signals while being connected to the steering wheel docking station 200, driving related information measured by sensors within the vehicle or information obtained from sensors installed in the driver's smart phone or other electronic devices may be transmitted to the automotive key device 100. In addition, body signal information and information about the situation at the time of collecting body signals may be stored and utilized in association with each other. In this case, when the collected body signals of the driver are transmitted to an external server via the communicator, the information about the situation at the time of collecting the body signals may also be transmitted. Therefore, the situation the driver is in may be identified from more diverse aspects, and an emergency situation can be dealt with more effectively.

As described hereinabove, multi-body signal measuring sensors in an automotive key device are thus always carried by a driver. Therefore, the driver may easily measure his or her body signals. In addition, the automotive key device may be connected to a vehicle, more specifically, to a docking station of a steering wheel on which both hands of the driver are placed naturally while driving. Therefore, the driver's body signals may be measured more easily and accurately.

Further, the driver's measured body signals may be utilized for various purposes using a system formed by devices, such as a navigation device, an automotive personal computer (PC), a communicator, etc. provided within the vehicle, together with the automotive key device and the steering wheel docking station. In particular, if it would be dangerous for the driver to continue driving based on the driver's measured body signals, a feedback signal may be transmitted to the system through the communicator to warn the driver. In addition, the feedback signal indicating an emergency situation may be transmitted to an emergency rescue center together with a GPS signal of the vehicle. Therefore, the emergency situation can be effectively handled. However, the effects of the present invention are not restricted to any of the effects set forth herein. The above and other effects of the present invention will become more apparent to one of ordinary skill in the art to which the present invention pertains by referencing the claims.

While exemplary embodiments of the present invention have been described with reference to the accompanying drawings, it will be understood by those of ordinary skill in the art that various changes in form and details may be made therein without departing from the spirit and scope of the present invention. The exemplary embodiments should be considered in a descriptive sense only and not for purposes of limitation.

What is claimed is:

1. A steering wheel docking station to which an automotive key device is connected, wherein the automotive key device is connected, in the form of a holder, to or merged with a mechanism of opening or shutting an automotive door and includes an ECG sensor having a first body signal electrode and a second body signal electrode and a contact terminal electrically connected to the ECG sensor, the steering wheel docking station comprising:
   one or more replacement electrodes separate and distinct from the body signal electrode and the second body signal electrode, the one or more replacement electrodes being configured to replace functions of one or both of the first body signal electrode and the second body signal electrode of the automotive key device; and
   a receptacle configured to removeably and replaceably receive the automotive key device therein,
   wherein the contact terminal is configured to serve as a passage for electrical connection with devices within a vehicle, and
   wherein the replacement electrodes (i) are configured to transmit signals from a driver's hands on a steering wheel to the automotive key device through the contact terminal such that the driver's ECG information can be obtained and (ii) are disposed at locations where the driver's hands are placed while driving.

2. The steering wheel docking station of claim 1, wherein when the driver's body signal information collected while the automotive key device is connected to the steering wheel docking station is transmitted to the automotive key device via the contact terminal, driving related information measured by sensors within the vehicle or information obtained from sensors installed in the driver's smart phone (i) is configured to be transmitted to the automotive key device via the contact terminal and is configured to be stored in the automotive key device in association with the driver's body signal information.

3. The steering wheel docking station of claim 2, wherein the driver's body signal information and the driving related information are transmitted simultaneously.

4. The steering wheel docking station of claim 1,
   wherein none of the first body signal electrode and the second body signal electrode of the automotive key device is exposed when the automotive key device is inserted into the receptacle, and
   wherein two replacement electrodes are configured to obtain body signals in place of the first body signal electrode and the second body signal electrode of the automotive key device, respectively.

5. The steering wheel docking station of claim 1,
   wherein one or both of the first body signal electrode and the second body signal electrode of the automotive key device are configured to be exposed when the automotive key device is inserted into the receptacle, and
   wherein one replacement electrode is configured to obtain body signals in place of one of the first body signal electrode and the second body signal electrode of the automotive key device.

6. The steering wheel docking station of claim 5, wherein all of the first body signal electrode and the second body signal electrode of the automotive key device are exposed, and
   wherein the other body signal electrode whose functions are not replaced by the replacement electrode from among the first body signal electrode and the second body signal electrode of the automotive key device is configured to eliminate a common phase in order to remove noise generated while the vehicle is being driven.

7. A system comprising:
   an automotive key device (i) connected, in the form of a holder, to a mechanism of opening or shutting an automotive door or merged with the mechanism of opening or shutting the automotive door and (ii) including an ECG sensor having:
      a first body signal electrode,
      a second body signal electrode, and
      a contact terminal electrically connected to the ECG sensor;
   a steering wheel docking station including (i) one or more replacement electrodes configured to replace functions of one or both of the first body signal electrode and the second body signal electrode of the automotive key device, and (ii) a receiver configured to removably and replaceably receive the automotive key device therein; and
   an automotive navigation device or personal computer (PC) electrically connected to the steering wheel docking station,
   wherein the contact terminal is configured to serve as a passage for electrical connection with devices within a vehicle,
   wherein the first and second body signal electrodes of the automotive key device are configured to be inoperable upon the automotive key device being received in the receiver, and the replacement electrodes of the steering wheel docking station (i) are configured to transmit signals from a driver's hands on a steering wheel of the vehicle to the automotive key device through the contact terminal such that the driver's ECG information can be obtained and (ii) are disposed at locations where the driver's hands are placed while driving,
   wherein the steering wheel docking station is configured to provide body signal information including ECG information obtained by the automotive key device to the automotive navigation device or PC, and
   wherein the body signal information is stored in the automotive navigation device or PC or configured to be used as a basis for providing other body signal information through an arithmetic operation.

8. The system of claim 7, wherein the automotive key device further includes:
   a PPG sensor; and
   a SpO$_2$ sensor, wherein the PPG sensor and the SpO$_2$ sensor are electrically connected to the contact terminal, and wherein the automotive navigation device or PC is configured to calculate the driver's blood pressure information based on the body signal information including ECG, PPG and SpO$_2$ information obtained from the automotive key device and is configured to store the calculated blood pressure information.

9. The system of claim 8, wherein the automotive navigation device or PC includes a display, and wherein the display is configured to display the body signal information obtained from the automotive key device or the blood pressure information calculated based on the body signal information.

10. The system of claim 7, further comprising:
a communicator, wherein the communicator is configured to transmit the body signal information obtained from the automotive key device or the blood pressure information calculated based on the body signal information to an external server.

11. The system of claim 10, wherein when the driver's body signal information collected while the automotive key device is connected to the steering wheel docking station is transmitted to the automotive key device via the contact terminal, driving related information measured by sensors within the vehicle or information obtained from sensors installed in the driver's smart phone is also transmitted to the automotive key device via the contact terminal and stored in the automotive key device in association with the driver's body signal information, and wherein when the body signal information obtained from the automotive key device or the blood pressure information calculated based on the body signal information is transmitted to the external server via the communicator, the information stored in association with the body signal information is also transmitted to the external service via the communicator.

12. The system of claim 11, wherein the driver's body signal information collected while the automotive key device is connected to the steering wheel docking station and the driving related information are transmitted simultaneously, and wherein the body signal information obtained from the automotive key device or the blood pressure information calculated based on the body signal information and the information stored in association with the body signal are transmitted simultaneously.

13. The system of claim 10, wherein the communicator is further configured to receive a feedback signal to the body signal information or the blood pressure information calculated based on the body signal information from the external server, wherein the system is configured to alert the driver or to put the vehicle in an emergency driving mode based on the feedback signal, and wherein the communicator is further configured to transmit the feedback signal to a server of an emergency rescue center together with global positioning system (GPS) information of the vehicle.

14. An automotive system for use with an automotive vehicle, comprising:

an automotive key device, the automotive key device, the automotive key device having an electrocardiogram (ECG) sensor with at least a first body signal electrode and a second body signal electrode, and the automotive key device having a contact terminal electrically connected to the ECG sensor, the contact terminal being configured to serve as a passage for electrical connection with devices within the automotive vehicle;

a steering wheel docking station configured to connect with the automotive key device, the steering wheel docking station including one or more replacement electrodes configured to replace functions of the first and second body signal electrodes of the automotive key device, the one or more replacement electrodes (i) being configured to transmit body signals from a driver's hands on a steering wheel of the automotive vehicle to the automotive key device through the contact terminal and (ii) being disposed at locations where the driver's hands are placed while driving; and a receptacle on the steering wheel docking station configured to receive the automotive key device therein, wherein at least one of the first or second body signal electrodes is configured to become inoperable when the automotive key device is received into the receptacle, and wherein at least one of the one or more replacement electrodes is configured to obtain body signals of the driver in place of the at least one inoperable first or second body signal electrodes of the automotive key device.

15. The automotive system claim 14, further comprising:
a photoplethysmography (PPG) sensor on the automotive key device; and
a saturation of peripheral oxygen (SpO$_2$) sensor on the automotive key device,
wherein the PPG sensor and the SpO$_2$ sensor are electrically connected to the contact terminal.

16. The automotive system claim 14, further comprising:
a memory configured to store measured body signals.

17. The automotive system claim 14, wherein none of the first body signal electrode and the second body signal electrode of the automotive key device are exposed when the automotive key device is inserted into the receptacle, and wherein two replacement electrodes of the one or more replacement electrodes are configured to obtain body signals in place of the first body signal electrode and the second body signal electrode of the automotive key device, respectively.

* * * * *